United States Patent [19]

Rochkind et al.

[11] Patent Number: 4,966,144
[45] Date of Patent: Oct. 30, 1990

[54] METHOD FOR INDUCING REGENERATION OF INJURED NERVE FIBERS

[76] Inventors: Simeone Rochkind, 5 Kashani St.; Liliane Barr-Nea, 5 Debora Hanevia St.; Rachel Lubart, 10 Hankin St., all of Tel Aviv, Israel

[21] Appl. No.: 204,207

[22] Filed: Jun. 8, 1988

[30] Foreign Application Priority Data

Jun. 9, 1987 [IL] Israel ............................................ 82830

[51] Int. Cl.$^5$ ................................................ A61N 5/00
[52] U.S. Cl. ..................................... 128/395; 128/398
[58] Field of Search ................................ 128/345–398, 128/303.1

[56] References Cited

U.S. PATENT DOCUMENTS 4,671,285  6/1987  Walker ................................ 128/395

FOREIGN PATENT DOCUMENTS 2740969  3/1979 · Fed. Rep. of Germany ...... 128/398

OTHER PUBLICATIONS

Rochkind, S. (1978), Stimulation Effect of Laser Energy on the Regeneration of Traumatically Injured Peripheral Nerves, The Krim National Medical Inst., Morphogensis and Regenerations 73: 4850.
Das, G. D. (1983), Neural transplantation in the spinal cord of adult rats, J. Neurol. Sci. 62: 191–210.
Wolman, L. (1967), Post-traumatic regeneration of nerve fibers in the human spinal cord and its relation to intramedulatory neuroma, J. Path. Bact. 94: 123–129.
De La Torre, J. C. (1981), Spinal cord injury, Review of basic and applied research, Spine 6: 315–335.
Barret, C. P., et al. (1984), Differences between adult and neonatal rats in their astroglial response to spinal injury, Exp. Neurol. 84: 374–385.
Richardson, P. M., et al. (1984), Peripheral injury enhances central regeneration of primary sensor neurons, Nature 309: 791–792.
Reier, P. J., et al. (1986), Intraspinal transplantion of embryonic spinal cord tissue in neonatal and adult rats, J. Compar. Neurol. 247: 275–296.
Richardson, P. M. et al. (1980), Axons from CNS neurons regenerate into PNS graft, Nature 1980; 284: 264–265.
Aguayo, A. J., et al. (1983), A potential for axonal regeneration in neurons of the adult mammalia nervous system, Birth Defects; Original Article Series 19: 327–340.
Wrathall, J. et al. (1982), Reconstruction of the contused cat spinal cord by the delayed nerve graft technique and cultured peripheral non–neuronal cells, Acta Neuropathol Berl 57: 59–69.
Rochkind, S., et al. (1986), Electrophysiological effect of HeNe laser on normal and injured sciatic nerve in the rat, Acta Neurochir (Wien) 83: 125–130.
Nissan, M., et al. (1986), HeNe laser irradiation delivered transcutoneously; its effect on sciatic nerve of rats, Laser. Surg. Med. 6: 435–438.
McKibbin; A Preliminary study on the Effects of a Helium–Neon Laser on Nerve Regeneration and Collateral Nerve Sprouting After Denervation in Rats, 1985; Abstract from American Society for Laser Medicine and Surgery Abstracts, p. 185.

Primary Examiner—William H. Grieb
Assistant Examiner—Mark S. Graham
Attorney, Agent, or Firm—Steinberg & Raskin

[57] ABSTRACT

Light irradiation having a wavelength of 380–1200 nm was found to have beneficial healing properties on the nervous system.

By the method, the regeneration of an injured spinal cord is induced by transplanting a nerve graft into an injured site of the spinal cord and post-operatively irradiating with light having the above specified wavelength.

15 Claims, No Drawings

METHOD FOR INDUCING REGENERATION OF INJURED NERVE FIBERS

FIELD OF INVENTION

The invention concerns treatment of neural injuries by surgery combined with post operative light irradiation. The invention is further concerned with a light device, such as a laser, which is suitable for use in such a treatment.

BACKGROUND OF THE INVENTION AND PRIOR ART

The following references are relevant prior art for the subject matter of the present invention:

1. Barnett C. P., Donati E. J., Gath L. (1984), Differences between adult and neonatal rats in their astroglial response to spinal injury, Exp. Neurol 84:374–385.
2. Wolman L. (1967), Post-traumatic regeneration of nerve fibers in the human spinal cord and its relation to intramedulatory neuroma. J.Path.Bact. 94:123–129.
3. Young J. S., Northup N. E. (1979), Statistical information pertaining to some of the most asked questions about spinal cord injury. Sci Digest 1:11.
4. De La Torre J. C. (1981), Spinal cord injury. Review of basic and applied research. Spine 6:315–335.
5. Collins W. F. (1983), A review and update of experimental and clinical studies of spinal cord injury. Paraplegia 21:204–219.
6. Aguayo A. J., Benfey M. and David S. (1983), A potential for axonal regeneration in neurons of the adult mammalia nervous system. Birth Defects: Original Article Series 19:327–340.
7. David S. and Aguayo A. J. (1985), Axonal regeneration after crush injury of rat central nervous system fibres innervating peripheral nerve grafts; J. Neurocytol 14:12.
8. Rochkind S. (1978), Stimulation effect of laser energy on the regeneration of traumatically injured peripheral nerves. The Krim National Medical Inst., Morphogenesis and Regenerations 73:48–50.
9. Nissan M., Rochkind S., Razon N. and Bartal A. (1986), HeNe laser irradiation delivered transcutoneously: its effect on sciatic nerve of rats. Laser. Surg. Med. 6:435–438.
10. Rochkind S., Nissan M., Razon N., Schwarts M. and Bartal A. (1986), Electrophysiological effect of HeNe laser on normal and injured sciatic nerve in the rat. Acta Neurochir (Wien) 83:125–130.
11. Richardson P. N., McGuinness U. M., Aguayo A. I. (1980), Axons from CNS neurons regenerate into PNS graft. Nature 1980; 284:264–265.
12. Wrathall J., Rigamonti D. D., Bradford M. R., Kao C. C. (1982), Reconstruction of the contused cat spinal cord by the delayed nerve graft technique and cultured peripheral non-neuronal cells. Acta Neuropathol (Berl) 57:59–69.
13. Das G. D. (1983), Neural transplantation in the spinal cord of adult rats. J. Neurol. Sci. 62:191–210.
14. Richardson P. M., Issa V. M. K. (1984), Peripheral injury enhances central regeneration of primary sensor neurons. Nature 309:791–792.
15. Reier P. J., Bergman B. S., Wujek J. R. (1986), Intraspinal transplantation of embryonic spinal cord tissue in neonatal and adult rats. J. Compar. Neurol. 247:275–296.

Nerve fibres in the central nervous system of mammals in general, and humans in particular, are incapable of spontaneous complete regeneration after injury and consequently any paraplegia resulting from spinal cord injury is permanent. The inability of the spinal cord to regenerate is attributed mainly to large cicatrices which are formed by the glial scar present at the site of injury (Ref. 1 and 2).

Peripheral nerve fibres, on the other hand, do regenerate in many cases, thereby restoring motor and sensory functions. However their regeneration, apart from not always being complete, progresses at a rather slow rate.

Spinal cord injuries are among the major clinical problems encountered in neurological and neurosurgical wards (Ref. 3). Therefore, it has been the object of extensive research throughout the world to find methods for inducing the restoration of motor functions paralysed upon injury of the spinal cord, so far, however, to no avail (Ref. 4 and 5). Thus, while it was demonstrated in rats whose spinal cords were experimentally transected that nerve fibres can grow through an autologous peripheral nerve graft transplanted into the site of injury, such growth did not bring about the desired restoration of motor functions (Ref. 6 and 7).

It has already been suggested that the regeneration of injured peripheral nerves can be accelerated by low energy laser irradiation applied to the injured nerve (Ref. 8). Thus, Rochkind et al. (Ref. 9, 10) demonstrated that trancutaneous low energy laser irradiation of the sciatic nerve induced an increase in the amplitude of the electrical signals recorded in the irradiated nerve, i.e. increasing the size of the action potential.

SUMMARY OF THE INVENTION

The present invention has three aspects, the first of which concerns the initiation of regeneration of motor activity at an injured site of a spinal cord by a combination of transplantation of a nerve graft into the injured site of the spinal cord and irradiation by a low energy light at said site. Apart from the fact that it never occurs spontaneously, no method for the induction of this healing process has ever been found prior to the present invention.

In its second aspect the present invention concerns the acceleration of regeneration of function of an injured peripheral nerve by irradiation of the corresponding spinal cord segment with a low energy light source. This irradiation may be performed in conjunction with a neurosurgical or any other treatment of the injured peripheral nerve.

The third aspect of the present invention concerns direct irradiation of the exposed nerve for a certain time during surgery in order to prevent or diminish the disruption in the nerve's ability to conduct nerve-impulse, which may be caused by accidentally damaging the nerve.

GENERAL DESCRIPTION OF THE INVENTION

In the following description and claims, the term "functional regeneration" will be used to denote such spinal nerve fibre regeneration which results in the recovery of motor activity. In connection with injuries to the spinal cord, the term "proximal" will be used to denote that side of the injury which remains functionally connected to higher levels of the spinal cord and to the brain, while the term "distal" will be used to denote that side of the injury which, owing to the injury, becomes functionally disconnected therefrom. Thus, the proximal side of an injury is the side which retains its motor function, i.e. motor organs connected thereto remain functional whilst, in contrast, organs which are connected to the distal part of an injury become paralyzed.

The present invention is based on three surprising findings:

(i) transplantation of a nerve graft into an injured spinal cord area in combination with post operative light irradiation leads to functional regeneration of injured nerve fibres in the spinal cord;

(ii) the regeneration of an injured peripheral nerve is accelerated when the region of the spinal cord from which this peripheral nerve originates is irradiated with light;

(iii) direct irradiation of an exposed injured peripheral nerve increases the rate by which its ability to transmit neural impulses is restored, and if the irradiation is performed prior to damaging the nerve, the disruption of the nerve's ability to conduct impulses is greatly diminished or even prevented.

Thus, in accordance with the first aspect of the present invention there is provided a method of inducing functional regeneration of nerve fibres at an injured site of the spinal cord, comprising exposing said injured site and grafting a segment of a nerve (hereinafter "graft") in such a way that the graft's longitudinal axis is parallel to the spinal cord's longitudinal axis and that said graft is in contact with both the proximal and distal uninjured spinal cord tissue suturing the dura, muscle, fascia, and skin, and post operatively irradiating the so grafted area of the spinal cord with a light source generating light at a wavelength being within the range of 380–1,200 nm.

It is preferred, in accordance with the first aspect of the present invention, that in addition to post operative irradiation the grafted area will also be irradiated directly for a certain time during the operation, prior to suturing the dura, muscle, fascia and skin, with light being within the same wavelength range as above. It was found that such direct irradiation accelerates the functional regeneration of the spinal cord nerve fibres.

As is well known in the art, there is hardly any immune response against foreign grafts in the nervous system. Consequently, although the use of autologous nerve grafts is generally more practical, heterologous nerve grafts may also be used to advantage in the performance of the method in accordance with the first aspect of the present invention. Accordingly, in practising the present invention, "nerve graft banks" may be established from which stretches of heterologous nerves may be obtained for the functional regeneration of spinal cord nerve fibres by transplantation and irradiation as specified.

The graft is preferably a segment of a peripheral nerve, which peripheral nerve may, for example, be a sciatic nerve, a sural nerve or a glossopharyngeal nerve. However, in complete contrast to what might have been expected, it was found in accordance with the present invention that also spinal cord segments may be used as the graft. It is obvious to those skilled in the art that grafting a spinal cord segment into an injured site or the recipient spinal cord may be practical only when the graft is heterologous. A peripheral nerve segment may however be both autologous and heterologous.

In the performance or the method according to this first aspect of the present invention when grafting a segment of a peripheral nerve, the epineurium is preferably removed from the nerve segment to be transplanted.

In accordance with the second aspect of the present invention, the spinal cord is irradiated with light of the above specified wavelength in order to accelerate regeneration of an injured peripheral nerve. In accordance with this aspect, the segments of the spinal cord which are irradiated are those which correspond to the peripheral nerve, i.e. the ones from which said peripheral nerve originates. The irradiated light reaches the spinal cord through the space between the vertebrae which is filled with cartilage tissue which readily transmits light. The irradiated light may also be so targeted as to be primarily directed at said space. The irradiation of light may be performed at a single instant or repeatedly, i.e. for a certain time each day on several consecutive days. This treatment may also be effected in conjunction with a neurosurgical operation to the peripheral nerve or in conjunction with treatment in accordance with the third aspect of the present invention.

In accordance with a third aspect of the present invention, a peripheral or cranial nerve is irradiated directly with a low energy light having the above specified wavelength. This irradiation may be performed during operations which involve the exposure of a peripheral or a cranial nerve, such as various orthopedic and neurological surgeries, which exposure may result in injury to to said nerves. It was found in accordance with the present invention that such irradiation performed prior to experimental injury of the nerve surprisingly brought about a significant decrease in the conduction block in the nerve caused by said injury.

While it is advantageous to perform the method according to a first embodiment of the present invention soon after injury, it is also possible to perform the method to advantage on subjects suffering from a long standing spinal cord injury.

The light source which is employed for irradiation at the grafted area according to this embodiment may either be a coherent or a non-coherent light source.

As shown by Nissan et al. (Ref. 9) a fair fraction of the irradiated light penetrates the skin and muscle tissue. Accordingly, in accordance with a first embodiment of both first and second aspects of the present invention, the post operative irradiation is effected transcutaneously. However, as known, the fraction of the light which penetrates the skin and muscle and reaches the grafted area is generally reduced with lowering the wavelength of the irradiated light; in particular, light penetration is reduced considerably below a wavelength of 600 nm. Accordingly, when practicing this embodiment of the present invention, the intensity of the irradiated light has to be increased with lowering its wavelength. However, care must be taken not to excessively increase the light's intensity, which may cause burning of the skin.

The light beam in accordance with either of the three aspects of the present invention can either be maintained in a stationary position or moved along the irradiated area, in order to irradiate the full length thereof. A moving beam can have a higher maximal light intensity than a stationary beam without causing tissue burns and is therefore especially suitable when the irradiation is transcutaneous, in accordance with said first embodiment, thus enabling a higher light flux to reach the neural tissue. Irradiating the full length of the area to be irradiated may also be achieved by splitting the emitted light into a multitude of beams, e.g. by an optical cable having a single light input and a multitude of light outputs, and arranging the beams so as to obtain an array of light spots along the grafted area.

In accordance with a second embodiment of the method according to both the first and second aspects of the present invention, the irradiation is targeted directly onto the grafted area by means of optical fibres which are suitably introduced in the course of operation. Since absorption of light by the overlaying tissue is avoided, considerably lower light intensities may be employed, thereby avoiding tissue burn.

By one mode of practising the above three aspects of the invention, irradiation is performed continuously for a certain time on each of several consecutive days after the operation; this mode will be referred to hereinafter as the "continuous mode".

When the continuous mode is applied in practising said first embodiment of the method according to the present invention, the intensity of the irradiated light should be below 100 J/cm$^2$, in order to avoid excessive heating of the skin. If a moving light beam is used, the intensity thereof may be increased up to 1000 J/cm$^2$. Thus, for example, where a laser source is used in practicing this embodiment of the present invention the intensity thereof should be below 60 mW, if the light beam is stationary and below 500 mW, if the light is moving. Suitable light sources for such an irradiation are HeNe type laser, generating light at a wavelength of 632 nm having a light intensity of about 16 mW, and C.W.Ar type laser generating light at 465 or 520 nm having a light intensity of about 40 mW.

When the continuous mode is applied in practising said second embodiment of the method according to the present invention, the intensity of the irradiated light may be much lower than in said first embodiment. Suitable intensities for achieving functional regeneration by the continuous mode are of the order of 0.05–15 J/cm$^2$. Thus, for example, when a continuous laser light source is used in practising this second embodiment of the present invention the intensity thereof should be in the order of 0.03–1.0 mW.

It was found, in accordance with the present invention, that very good results of functional regeneration are obtained with irradiations of light having a wavelength of about 540 nm. However, as already mentioned above, light having this wavelength does not readily penetrate the skin and muscle tissue and therefore light of this wavelength cannot be used when practising the continuous mode of the present invention for transcutaneous irradiation in accordance with said first embodiment. Such a light may, however, be irradiated directly onto the grafted area or injured spinal cord by targeting in accordance with said second embodiment of the present invention.

By another mode of practising the method according to one of the above three aspects of the invention, the irradiation is pulsed and this mode will be referred to hereinafter as the "pulsating mode". In practising the pulsating mode, the likelihood of the formation of burns is lower than in the continuous mode and it is accordingly possible to use in this mode higher intensity irradiation, which is of particular advantage when the irradiation is effected transcutaneously in accordance with the first embodiment of the first and second aspects of the present invention.

The pulsating mode is particularly suitable for transcutaneous irradiation of light of wavelength below 600 nm in general and of light of wavelength of about 540 nm in particular. Such light, as mentioned above, does not readily penetrate the skin and therefore higher intensities are needed, which intensities can be achieved in this mode without causing burns.

A further advantage of the pulsating mode is that the use of higher light intensities will enable the shortening of the treatment time. In practising the pulsating mode it is possible to use, for example, a pulse dye laser, generating light at a wavelength of 588 nm. Typically, the pulse duration may be of the order of about 10 ns and the frequency of the order of about 10 Hz. In the pulsating mode, if irradiation is effected transcutaneously in accordance with said first embodiment, the intensity can be increased up to about 10 kJ/cm$^2$ and where, for example, a laser light source is used the average power thereof can be up to about 1–1.5 w, with a pulse peak power of 1 kW–1 mW.

The invention also provides for use in the performance of the above specified methods, an apparatus adapted for irradiation of living subjects and comprising at least one light source emitting light at a wavelength within the range of 380–1,200 nm. It is preferred that the light source will emit light at a wavelength within the range of 450–1000 nm, and most preferred within the range of 450–650 nm. In accordance with one embodiment of such apparatus, the light source is adapted for continuous emission. In accordance with another embodiment of such apparatus, the light source is adapted for pulsating emission.

When the apparatus comprises two or more light sources, some may be adapted for continuous and others for pulsating operation.

The apparatus may comprise a coherent or a noncoherent light source or a combination of both.

The apparatus may optionally comprise also means of distributing the light generated along the grafted area. Such distributing means may, for example, be means of moving the beam along the grafted area, or means of splitting the generated light in order to obtain a multitude of light beams arrayed along the grafted area, e.g. by means of an optical cable having a single light input and a multitude of outputs.

Where the light source is not a laser, the apparatus should preferably comprise also focusing means for the light beam.

By yet another aspect, the invention provides an apparatus as specified in combination with instructions for the performance of post operative irradiation of a grafted nerve in the spinal cord of a living subject.

Axonal regeneration in the central nervous system following implantation of peripheral neural tissue has been reported in several animal species (Ref. 6.7 and 11 to 15). However, surprisingly and in complete distinction therefrom, in accordance with the above described first embodiment of present invention the physical growth of the spinal cord nerve fibres is accompanied by a functional regeneration. Thus, a universally long felt need is for the first time fulfilled in accordance with the first aspect of the present invention.

The second aspect of the present invention constitutes a significant unobvious enrichment of the art by providing an improved method for inducing functional regeneration of peripheral or cranial nerve.

By the method of the third aspect of the present invention, it is for the first time possible to prevent or diminish conduction failure of a peripheral or cranial nerve, which may be caused by accidental damage during an operation.

EXPERIMENTAL RESULTS

In the following, some experimental results are given to demonstrate conclusively that the method according to the invention indeed brings about functional regeneration of an injured spinal cord and improved regeneration of an injured peripheral nerve, as specified. The results reported below were obtained from dogs or rats, whose spinal cords or peripheral nerves were experimentally damaged to mimic naturally occurring spinal cord injuries, i.e. through accidents.

TEST NO. 1

15 dogs weighing from 10 to 15 kgs. were operated on in the following way:

1. Anaesthesis by an intravenous injection of nembutal (15 mg/kg body weight);
2. Exposure of the spinal cord between vertebra D11 to L1 by laminectomy and opening of the dura;
3. Transection of the spinal cord using 2 forceps;
4. Excision of a fragment of the sciatic nerve from the middle thigh region of the left hind leg;
5. Grafting the fragment of the sciatic nerve after removal of its epineurium into the transected spinal cord in such a way that its longitudinal axis coincides with the longitudinal axis of the spinal cord and that its two ends are in contact with uninjured tissue in the two ends of the transected area;
6. Suturing the dura;
7. Suturing the muscles, fascia and skin;
8. Stitching the proximal stump of the cut sciatic nerve to the distal stump.

After the operation the dogs were divided into two groups, the first consisting of 10 dogs wherein each dog received transcutaneous spinal irradiation with a continuous He-Ne laser (16 mW, 30 minutes) at 7 consecutive points along the wound for 20 consecutive days starting immediately after the operation, and the second consisting of 5 dogs, serving as control.

Following the operation, each dog was injected daily with 4 million units of penicillin for the first 20 days following the operation.

One month after the operation, the animals were anaesthetised, the vertebral column was removed, cut into fragments and put into a solution of 10% of formaline. The spinal cord fragments were then separated from the vertebrae and embedded in paraplast. Transverse sections of six microns were then cut and stained with hematoxylin-eosin and luxol. Serial sections were made through the whole region of the graft-transection area. The sections were viewed with a light microscope.

RESULTS

Four-seven weeks after the operation the nine remaining animals (one animal died of pneumonia) showed first signs of functional regeneration. This functional regeneration was evidenced by the restoration of motor functions that had disappeared in consequence of the transection. Thus, the dogs were able again to control urination and stand on their right leg for a few seconds (the left leg was paralysed since the sciatic nerve has been cut and a piece thereof was used as the graft).

The following morphological picture was observed:
(1) Transection-transplant region:
30 Day post-surgery, the remnants of sciatic nerve were observed in this region. In the control, non-irradiated, dogs, the spinal cord and the peripheral nerve implant showed signs of destruction, the organization of the transplant was not retained and Schwann cells phagocytosing debris of axons and myelin were evident. On the other hand, in the dogs that had received laser treatment, there was less destruction of spinal cord tissue and greatly diminished gliosis (scar) of the implant, new axons were seen in the region of the degenerated peripheral nerve.

(2) Distal Region

In control, non-irradiated animals, the general organization of the tissue was degenerated with extensive damage to motor neurons, evidence by chromatolysis and cytoplasmic atrophy. In contrast thereto, in the laser-treated animals, the general organization of the spinal cord tissue was retained and most of the perikarya in this region appeared normal with well-defined nuclei, nucleoli and Nissl bodies.

An important finding in the irradiated dogs was the growth of many capillaries coming from the anterior horn and from the myelin which invaded the graft-transection region, which growth is an important factor in supporting regeneration of nerve fibres.

The greatly diminished scar is a very important finding, inasmuch as its presence has been recognized as one of the factors hindering new axon elongation in the central nervous system and indeed numerous, new axons were seen in the graft region of the laser-treated group.

It may be concluded that the stimulatory effects of laser irradiation combined with PNS transplant mitigates the damage following transection and thus accounts for survival of most of the treated dogs, together with the progressive restoration of their locomotor function.

TEST NO. 2

This test was made in order to test the effect of a direct light irradiation on a nerve.

43 Sprague-Dawley rats, weighing 0.2–0.3 kg each were anaesthetized with intraperitoneal Nembutal 15 mg/kg. The right sciatic nerve was exposed under a surgical microscope (Zeiss Co.) and two pairs of specially made, hookshaped electrodes (platinum/platinum chloride) were attached to the nerve so as to isolate it from the underlying tissue. A Grass nerve-stimulator (Model Sye Grass Co., Quincy, Mass.) was used to stimulate the nerve (0.2V, 1Hz) via the 2 proximal electrodes, while the resulting compound section potential was recorded, using a Beckman Dynograph (Model RM, 700, Beckman Co.), via the 2 distal electrodes. (The compound action potential is the summed electrical activity of all nerve fibres.)

The peak-to-peak value of the compound action potential was measured. The normal compound action potential stabilized shortly after the introduction of the electrodes, and its constant value measured for 10 minutes, was recorded as the normal compound action potential (=100%) for all rats.

The rats were divided into 5 groups of unequal size and after measuring the normal compound action potential, each group was treated as follows:

Group A (10 rats): nerve crush only (control group);
Group B (8 rats): irridation for 7 minutes by 0.3 mW He-Ne laser (632.8 nm) at 10 consecutive points along the nerve followed by crushing the nerve.
Group C (16 rats): nerve crush followed by 7 minutes irradiation as in group B.

Group D (5 rats): same treatment as for Group B but a 17 mw He-Ne CW laser was used instead.

Group E (5 rats): the nerve was irradiated and the temperature thereof was measured using a needle thermistor (Yellow Springs 524).

The following results were obtained:

The control group (A) showed an expected sharp drop in electric activity following crush, the level stabilizing around 36% (S.D. 8%) of the normal, pre-crush level. The application of 0.3 mW laser irradiation to the rats of Groups B (delivering $0.13J/cm^2$ of energy to the ten irradiated points along the nerve), increased the compound action potential to approximately 150% of the normal value after 10 minutes. The crush (done after irradiation) caused an immediate decline in the electric acitivity, to 90% (S.D. 12%) of the normal value, but rose again and stabilized around 110% (S.D. 35%).

The initial decline of the compound action potential in Group C was similar to that of Group A. However, while in the control Group A it remained at that level, the use of low irradiation in Group C promoted a restoration of compound action potential to 70% (S.D. 30%) of the normal pre-crush value.

The use of excess energy on rats of Group D did not exert any significant effect on the compound action potential and the results were practically identical to those for the non-irradiated control Group A. This points to the existence of an optimal level to the useful energy, above which the light loses its stimulating effect.

In the temperature measurements in Group E, a change of no more than 0.1° C., during low-energy laser irradiation, was observed. This shows that the effect of light cannot be attributed to a heating effect.

These results prove that direct light irradiation has an immediate effect on recovery of activity and this suggest the beneficial use of direct irradiation during the operation in accordance with the present invention. Furthermore these results also show that irradiation of light on peripheral and cranial nerves during an operation where these are exposed may prevent damages which may be caused by the operation itself.

TEST NO. 3

The experiment of Test No. 2 was repeated with a laser emitting light at 540 nm substituting the He-Ne laser (632 nm), and an even stronger effect on the restoration of function than that at Test No. 2, was seen.

This experiment, apart from verifying the general advantage of direct presuturing, in addition demonstrates also the general better effect lower wavelengths have on functional regeneration.

TEST NO. 4

The effect of spinal irradiation on the regeneration of a crushed sciatic nerve was tested. 34 Three month old rats whose sciatic nerve was crushed were used for the study. The experimental procedure was as follows:

The rats were anesthetised by an intraperitoneal injection of 15 mg/Kg of nembutal. The thigh along the area of the sciatic nerve and the dorso-lumbar region of the spine were shaved. Next the sciatic nerves from both the left and right legs were exposed, separated from the surrounding muscle and crushed, using an ordinary closed haemostat for 30 sec., after which the incisions were sutured.

The rats were divided into two groups, one serving as control, and the other was subjected to transcutaneos irradiation of the spinal segments from which the crushed sciatic nerve originates ($L_4$–$S_2$). This irradiation was performed using a 16 mW CW HeNe delivering approximately $10^.J/cm^2$ to each of seven consecutive points along the overlaying skin. The irradiation was performed daily for 20 days following the crushing of the nerve.

Electrophysiological recordings were carried out in the sciatic nerve in order to determine the degree of regeneration. For that purpose the rats were anesthetised and two bipolar platinum needles were inserted transcutaneously near the sciatic nerve (care was taken to ensure the same needle depth in each case). The proximal needle was inserted into the hip and served for stimulating the nerve using a Grass Nerve Stimulator (Grass Co., Quincy, Mass. Model Sye) delivering 1V pulses at a frequency of 1Hz. The distal needle was inserted into the gastrocnemius muscle and served for recordng the compound potential using Dynograph type RM recorder 700 (Beckman Co.).

The first measurement in each animal was taken prior to the crush in order to obtain a normal, pre-crush value and subsequently measurements were made on days 1, 3, 7, 14, 21, 30, 45, 60, 90, 120, 180, 210, 240, 270, 300 and 330 after the operation. In each rat seven consecutive pulses were delivered and the compound action potential measured and their average amplitude determined.

The sciatic nerves of 5 control and 5 test animals were examined histologically. For that purpose these animals were anesthetised and than superfused with 3% gluteraldehyde through their heart. The sciatic nerves were then removed and divided into three segments—a proximal one, a middle one where the crush was made and a distal one—all of which were fixed in 2% gluteraldehyde and embedded in Epon (Shell Chemical Co., New York).

The following results were obtained:

In control, non-irradiated animals the sciatic nerve's compound action potential dropped to about 40% of control on the first day after crushing the nerve and further declined to about 20% after 20 days. Thereafter the amplitude of the compound action potential increased slowly and reached about 50% of control 330 days after crushing the nerve.

In irradiated animals the compound action potential decreased only slightly, to about 90% of control, one day after crushing the nerve and remained at about the same level throughout the 330 days tested, notwithstanding the fact that the irradiation treatment was limited only to the first 20 days.

Some of the results are summarized in the following Table 1:

TABLE 1

| Days After crush | Non-irradiated mean* | s.d** | Irradiated mean* | s.d** | p*** |
|---|---|---|---|---|---|
| 1 | 40 | 11 | 88 | 15 | <0.001 |
| 7 | 23 | 6 | 91 | 21 | <0.001 |
| 14 | 22 | 7 | 89 | 23 | <0.001 |
| 45 | 25 | 6 | 96 | 24 | <0.001 |
| 90 | 23 | 12 | 77 | 12 | <0.001 |
| 180 | 38 | 14 | 76 | 18 | <0.001 |
| 270 | 67 | 14 | 88 | 22 | <0.05 |
| 330 | 51 | 11 | 88 | 19 | <0.01 |

*mean - results given in % of control
**s.d - standard deviation
***p - probability, calculated by the two-tailed t-test.

It may be seen from the above results that the difference between the control and the experimental group is highly significant.

Histological comparison between the distal segment of the nerve from an irradiated animal to the distal nerve segment of a control, non-irradiated animal showed a more organized arrangement of the axons of the former. Thus for example, 45 days post-crush, the area distal to the crush in the irradiated animal contained mostly axons which had a thick sheath of myelin. In contrast thereto, the corresponding are in the control animals showed less organization with smaller and mostly non-mylinated fibres and numerous macrophages and phagocytes.

The general condition of the irradiated rats was much better than the non-irradiated ones, in that their hind legs were more functional. Additionally there were no trophic wounds in the irradiated rats whereas 20% of the control rats developed trophic ulcers. In the irradiated rats there was no side preference and the findings were simmilar for both legs.

The above results demonstrate the surprising effect that low energy light irradiation on the spinal cord has, in the introduction of healing of an injured peripheral nerve.

TEST NO. 5

Similarly as in Test No. 4, the sciatic nerve of 20 rats was experimentally crushed and thereafter the spinal cord was irradiated transcutaneously for 7 minutes on each of 20 consecutive days starting immediately after the crush was made. The rats were divided into four groups of 5 rats and each was irradiated by one of the following laser sources:

1. HeNe-laser—632 nm, 16 mW.
2. Pulsed dye laser—588 nm, 20 mW, 10 Hz.
3. C.W.AR-laser—520 nm, 40 mW.
4. C.W.Ar-laser—465 nm, 40 mW.

Thirty days after the operation, the animals were anaesthetised and the vertebral column was removed and prepared for light microscopy in a similar manner as in Test No. 1. In each case the degree the chromatolysis (which is the first stage in degeneration of nerve bodies following transection of a peripheral nerve), was determined. Furthermore, the number of Nissl bodies (which are organels associated with protein synthesis) in the nerve cell bodies, were also determined in each case.

The results show that the magnitude of the effect decreased with the decrease in the wavelength of the irradiated light. This decrease is caused by the lower penetration of light having a lower wavelength as explained above. As seen in Test 3, light having a lower wavelength has a stronger effect than light of a higher wavelength if irradiation is performed directly on the nerve.

TEST NO. 6

In 38 adult dogs, having an average weight of about 15 kg., a dorso-lumbar laminectomy of D10–L2 was performed, followed by transection of the spinal cord using two forceps. The dogs were divided into 6 groups with respect to the treament they received following the operation, as summarized in the following Table 2:

TABLE 2

| Group | No. of Dogs | Transplant of an uninjured segment of a sciatic nerve | Transplant of a crushed segment of a sciatic nerve* | Laser Irradiation |
|---|---|---|---|---|
| 1 | 4 | — | — | — |
| 2 | 4 | — | — | + |
| 3 | 6 | + | — | — |
| 4 | 6 | — | + | — |
| 5 | 6 | — | + | + |
| 6 | 12 | + | — | + |

*The sciatic nerve was crushed 10 days prior to the transplantation.
**He-Ne, 632.8 nm, 16 mW at 18J/cm$^2$ daily to each of seven points along the transplanted area.
Groups 1 to 5 were control groups and group 6 was treated in accordance with the invention. Transplantation of the sciatic nerve segment was performed in a similar manner as described in Toot 1.

The following results were obtained:

Group No. 1—The four dogs of this group remained paralegic and two of these dogs eventually died two weeks after the operation.

Group No. 2—The four dogs of this group survived for six months, but remained paralegic with no signs of mobility.

Group No. 3—The dogs survived for six months after the operation.

Group No. 4—The same results were observed as in group No. 3. This form of control was motivated by reports that upon grafting crushed segment stretched into injured peripheral nerves an enhanced regeneration of axons was observed. However, no such phenomenon was observed with nerve fibres of the spinal cord.

Group No. 5—Similar results as in groups Nos. 3 and 4, but after 3 months the dogs manifested a somewhat improved motility over the two previous groups.

Group No. 6—After one to two months, the dogs started to rise on their hind legs. After three months, these dogs were walking and after four months some were even jumping slightly and after six months the dogs were able to run for several minutes. However, the dogs were still somewhat weaker than normal, unoperated, dogs.

The above results demonstrate that only upon combination of grafting and post operative irradiation in accordance with the teaching of the present invention, functional regeneration of the nerve fibres is achieved.

The spinal cord of some of the tested dogs was examined histologically in a similar manner as in Test 1. In group 6 less separation of spinal and graft tissue and greatly diminished gliosis was observed, as compared to group 3. In both groups axons were seen to enter and traverse the graft after 3–6 months, the number increasing with time. However, the total number of axons in the laser treated group (group 6) was much larger than in the nonlaser treated group (group 3).

TEST NO. 7

This test was performed in order to demonstrate that a spinal cord segment can also serve as a graft in the performance of the method of the present invention for achieving a functional regeneration of the spinal cord.

Two spinal cord fragments from each of four donor dogs (total of eight fragments) were transplanted into the corresponding segment of each of 8 dogs, the spinal cord of which had been experimentally transected. The operational procedure of the transplantation was generally as follows:

1. Anesthesia by an intravenous injecton of 15 mg kg of nembutal
2. Laminectomy from vertebrae D10 to L2
3. Opening of the dura
4. Transplantation of the spinal cord fragments following removal of the corresponding segment from the dog's own spinal cord. Care was taken to ensure the exact orientation and position of the transplant
5. Suturinf of the dura
6. Suturing of the muscles, fascia and skin
7. Administration (to all dogs) of 0.5 g hydrocortisone daily for 10 days post operation and 6 million units of penicillin throughout the experiment.

The eight recipient dogs were then divided into two equal groups, one serving as unirradiated control, and the other irradiated daily through the closed skin for 20 consecutive days, starting immediately after the operation (He-Ne laser 16 mW), at $18J/cm^2$, at each of seven consecutive points along the transplanted area.

Three weeks after the operation the irradiated dogs were sacrificed, and perfused intracardially with 10% formalin. The spinal column was then removed and cut into three large fragments:
1. Proximal above the transplant
2. Transplant region
3. Distal below the transplant region The cord was then fixed in 10% formalin and freed from the vertebrae. Following fixation, the three segments were halved longitudinally and embedded in paraplast. Six $\mu$m sections were cut and stained with Hematoxylin-Eosin, luxol fast blue, and silver protein (Bodian's method).

The control unirradiated dogs died a few days after the operation with their spinal cord being completely necrotic. The irradiated dogs, on the other hand, survived.

The following histological picture was observed in the irradiated dogs: Transplant region: in the interface between the graft and the recipient spinal cord, no evidence of rejection such as excess lymphocytes or phagocytic cells was seen. Large cysts which are known to exist in such contact zones and which are believed to hinder nerve regeneration, were not seen. The graft itself seemed to have degenerated, which degeneration was apparent by the loss of organization, the disappearance of most of the neurons and axons, and in the abundance of scattered glial cells and leokyocytes. The border between the graft and the adjacent tissue was not sharply demarcated, suggesting some fusion of the two. The graft region was traversed by cords of glial tissue which formed a bridge linking the recipient tissues on both sides. Many capillaries were present within the graft and the pial tissues which are apparently newly formed, if judged by their relatively thin walls (endothelium only) and large lumen.

Depsite the evident degeneration of the transplant, it nevertheless contained also some normal-appearing axons. Proximal segment: the general organization was retained, the white matter appeared to be normal, but the grey matter contained some neurons and enlarged capillaries. There was also some increase in the number of glial cells. Distal segment: many of its axons degenerated and some of its myelin was destroyed. The grey matter contained numerous vacuoles, but also a few live neurons.

The above results shown that light irradiation not only prevents complete necrosis of the transplant, but even induces a nascence of regeneration as evident by new axons and blood capillaries.

Thus, these results demonstrate that also a spinal nerve graft can be used in the performance of the present invention. Additionally, the absence of an immune response against the graft demonstrates the beneficial use of a heterologous nerve graft in accordance with the present invention.

We claim:

1. A method of inducing functional regeneration of nerve fibres at an injured site of the spinal cord, comprising exposing said injured site, grafting into said injured site graft selected from the group consisting of peripheral nerves and spinal cord segments, in such a way that the graft's longitudinal axis is parallel to the spinal cord's longitudinal axis and that said graft is in contact with both the proximal and distal uninjured spinal cord tissue, suturing the dura, muscle, fascia and skin, and post operatively irradiating the so grafter area of the spinal cord with a light source generating light at a wavelength being within the range of 380–1200 nm.

2. A method of inducing functional regeneration of nerve fibres at an injured site of the spinal cord, comprising exposing said injured site, grafting into said injured site a graft selected from the group cosisting of peripheral nerves and spinal cord segment, in such a way that the graft's longitudinal axis is parallel to the spinal cord's longitudinal axis and that said graft is in contact with both the proximal and distal uninjured spinal cord tissue, irradiating said graft and the surrounding nerve tissue with a light source generating light at a wavelength being within the range of 380–1200 nm, suturing the dura, muscle, fascia and skin, and post operatively irradiating the so grafted area of the spinal cord with a light source generating light at a wavelength being within the range of 380–1200 nm.

3. A method according to claim 1 wherein the light source generates light at a wavelength being within the range of 450–1000 nm.

4. A method according to claim 3 wherein the light source generates light at a wavelength being within the range of 450–650 nm.

5. A method according to claim 1 wherein said light source is coherent.

6. A method according to claim 1 wherein said light source is non-coherent.

7. A method according to claim 1 wherein the irradiation of the spinal cord is performed transcutaneously.

8. A method according to claim 7 wherein the light beam generated by the light source is maintained in a stationary position over the grafted area, the light's intensity being below about 100 Joules/$cm^2$.

9. A method according to claim 8 wherein the generated light is split into a multitude of beams which are arranged so as to obtain an array of light spots along the grafted area.

10. A method according to claim 7 wherein the light beam about 1000 Joules/$cm^2$.

11. A method according to claim 1 wherein the irradiation is targeted directly onto the graft by means of optical fibres suitably introduced in the course of operation.

12. A method according to claim 11 wherein the irradiation of light is performed for continuous stretches of time and its intensity is in the order of 0.05–15 Joules/$cm^2$.

13. A method according to claim 9, wherein said light irradiation is performed in a pulsating manner, the intensity thereof being below about 10 KJoules/$cm^2$.

14. A method according to claim 13 wherein the wavelength of the irradiated light is below 660 nm.

15. A method according to claim 13 wherein the pulse duration is of the order of about 10 ns, its frequency is about 10 Hz, and its pulse peak power being below 1 MW.

* * * * *